United States Patent
Kobayashi et al.

(10) Patent No.: US 12,337,313 B2
(45) Date of Patent: Jun. 24, 2025

(54) STORAGE CONTAINER

(71) Applicant: FURUKAWA ELECTRIC CO., LTD., Tokyo (JP)

(72) Inventors: Go Kobayashi, Tokyo (JP); Junichi Hasegawa, Tokyo (JP); Noritaka Matsubara, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 990 days.

(21) Appl. No.: 17/397,272

(22) Filed: Aug. 9, 2021

(65) Prior Publication Data
US 2021/0362147 A1    Nov. 25, 2021

Related U.S. Application Data

(63) Continuation of application No. PCT/JP2020/004378, filed on Feb. 5, 2020.

(30) Foreign Application Priority Data

Feb. 13, 2019    (JP) .................................. 2019-023791

(51) Int. Cl.
*B01L 3/00*    (2006.01)
*B01L 99/00*   (2010.01)

(52) U.S. Cl.
CPC ......... *B01L 3/502* (2013.01); *B01L 2200/026* (2013.01); *B01L 2300/0832* (2013.01); (Continued)

(58) Field of Classification Search
CPC ......... B01L 2200/025; B01L 2200/026; B01L 2200/12; B01L 2300/0832;
(Continued)

(56) References Cited

U.S. PATENT DOCUMENTS 9,494,575 B2    11/2016   Jin et al.
9,977,017 B2     5/2018   Jin et al.
(Continued)

FOREIGN PATENT DOCUMENTS

JP    41 48367 B1    9/2008
JP    2011-128019 A  6/2011
(Continued)

OTHER PUBLICATIONS

International Search Report issued Apr. 21, 2020 in PCT/JP2020/004378, filed on Feb. 5, 2020, 3 pages.
(Continued)

*Primary Examiner* — Lydia Edwards
(74) *Attorney, Agent, or Firm* — Oblon, McClelland, Maier & Neustadt, L.L.P.

(57) ABSTRACT

A storage container includes: a substrate having a plurality of storage wells to store an object therein, the storage wells being formed on a predetermined substrate surface of the substrate. Further, the storage wells each includes an opening forming portion forming an opening portion opening on the substrate surface, and having an inclined surface that inclines from the substrate surface downward in a depth direction on an inner surface of the opening portion; and a bottomed storage portion that has a side wall surface extending in a direction perpendicular to the substrate surface on a lower side in the depth direction of the storage well relative to the opening forming portion, and that communicates with a region on the substrate surface through the opening portion, and a lower end of the inclined surface is connected to the side wall surface of the storage portion, forming a ridgeline.

6 Claims, 12 Drawing Sheets

(52) U.S. Cl.
CPC .................. *B01L 2300/0858* (2013.01); *B01L 2300/0877* (2013.01); *B01L 2300/0893* (2013.01); *B01L 2300/12* (2013.01)

(58) Field of Classification Search
CPC ..... B01L 2300/0858; B01L 2300/0877; B01L 2300/0893; B01L 2300/12; B01L 3/502; B01L 3/5085; C12M 1/34
See application file for complete search history.

(56) References Cited

U.S. PATENT DOCUMENTS

| | | |
|---|---|---|
| 2016/0137962 A1 | 5/2016 | Ejiri et al. |
| 2017/0023562 A1* | 1/2017 | Jin .................. G01N 33/54366 |

FOREIGN PATENT DOCUMENTS

| | | |
|---|---|---|
| JP | 2012-157267 A | 8/2012 |
| JP | 2014-110785 A | 6/2014 |
| JP | WO 2014/196204 A1 | 12/2014 |
| JP | 2017-63744 A | 4/2017 |
| WO | WO 2018/123663 A1 | 7/2018 |

OTHER PUBLICATIONS

Notice of Reasons for Refusal issued Jul. 20, 2021 in corresponding Japanese Application No. 2019-023791, 7 pages (with English translation).

* cited by examiner

STORAGE CONTAINER

CROSS-REFERENCE TO RELATED APPLICATION(S)

This application is a continuation of International Application No. PCT/JP2020/004378, filed on Feb. 5, 2020 which claims the benefit of priority of the prior Japanese Patent Application No. 2019-023791, filed on Feb. 13, 2019, the entire contents of which are incorporated herein by reference.

BACKGROUND

The present disclosure relates to a storage container.

In the related art, storage containers having plural wells (storage wells) to individually store minute objects to be stored, such as a cell, have been known. For example, when the object to be stored is a cell, a fluid (suspension) including 1.5 to 2.0 times as many cells as the number of storage wells arranged or more is poured onto a surface of a storage container, and cells are thus put into respective storage wells with the fluid. As such a storage well, for example, Japanese Patent No. 4148367 discloses a microwell in a form in which an opening of an inverted pyramid and a bottomed cylindrical hole are combined. Moreover, Japanese Laid-open Patent Publication No. 2014-110785 discloses wells in an inverted truncated pyramid shape formed in an immunochamber.

SUMMARY

There is a need for providing a storage container that is capable of suppressing an object to be stored getting damaged at the time of storage, and of improving the storage efficiency of the object to be stored in multiple storage wells.

According to an embodiment, a storage container includes: a substrate having a plurality of storage wells to store an object therein, the storage wells being formed on a predetermined substrate surface of the substrate. Further, the storage wells each includes an opening forming portion that forms an opening portion opening on the substrate surface, and that has an inclined surface that inclines from the substrate surface downward in a depth direction of the storage well on an inner surface of the opening portion; and a bottomed storage portion that has a side wall surface extending in a direction perpendicular to the substrate surface on a lower side in the depth direction of the storage well relative to the opening forming portion, and that communicates with a region on the substrate surface through the opening portion, and a lower end of the inclined surface is connected to the side wall surface of the storage portion, forming a ridgeline.

DETAILED DESCRIPTION

In the related art, in the storage well in the related art described in Japanese Patent No. 4148367, because a flat surface to place antibodies that are secreted from the stored cells is present between an inclined surface of the opening portion and a side wall surface of the well, an object to be stored can contact an edge of a portion at which this flat surface and the side wall surface are connected, and can be damaged when the object to be stored, such as a cell, is poured into the well.

Moreover, in the storage well in the related art described in Japanese Laid-open Patent Publication No. 2014-110785, because an inner wall surface of a well is inclined downward from an opening end toward the bottom surface, it is facilitated to pour an object to be stored into a well, but the object to be stored that has once been stored can be displaced out from the well with a flow of a fluid or the like. Because of this, a probability of the object to be stored being stored in the respective storage wells, that is, a ratio of the storage well in which the object to be stored is stored out of all the storage wells arranged in the storage container (herein referred to as storage efficiency) can be decreased.

Hereinafter, exemplary embodiments of a storage container according to the present disclosure will be explained in detail, with reference to the drawings. The embodiments are not intended to limit the present disclosure. Moreover, in the respective drawings, identical reference symbols are assigned to identical or corresponding components. Furthermore, the drawings are of schematic illustrations, and it is noted that a relationship in dimensions of the respective components and the like can be different from those in actual situations. Also among the drawings, portions in which a relationship and ratio in dimensions differ from one another can be included.

First Embodiment

Figure 1:
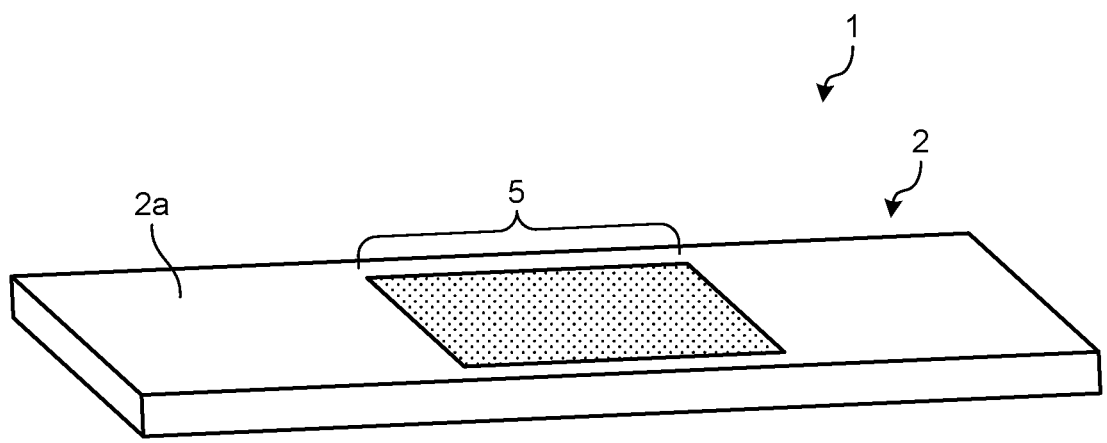
FIG. 1 is a diagram illustrating one configuration example of a storage container according to a first embodiment of the present disclosure.

A storage container according to a first embodiment of the present disclosure will be explained. FIG. 1 is a diagram illustrating one configuration example of the storage container according to the first embodiment of the present disclosure. A storage container 1 according to the first embodiment is a container to store a minute object to be stored, such as a cell, and is constituted of a substrate 2 in which a storage well group 5 is formed on a predetermined substrate surface 2a as illustrated in FIG. 1. The substrate 2 is, for example, a glass substrate that is made of a glass material, such as a silica glass ($SiO_2$). The storage well group 5 is constituted of multiple storage wells to store an object to be stored. These storage wells are formed to be arranged in a predetermined pattern, such as lattice, on the predetermined substrate surface 2a (upper surface in FIG. 1) in the substrate 2.

Figure 2:
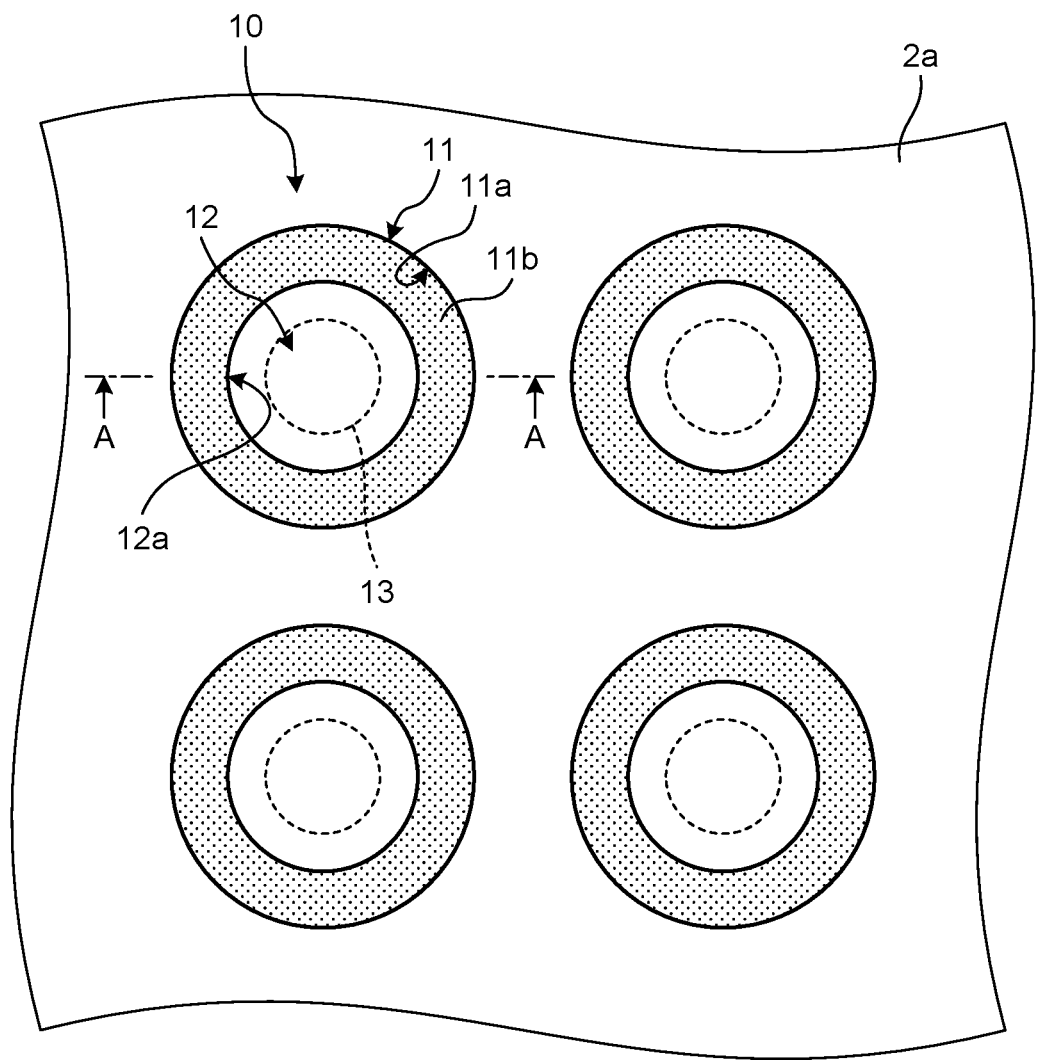
FIG. 2 is a diagram illustrating one configuration example of a storage well of the storage container according to the first embodiment of the present disclosure.
Figure 3:
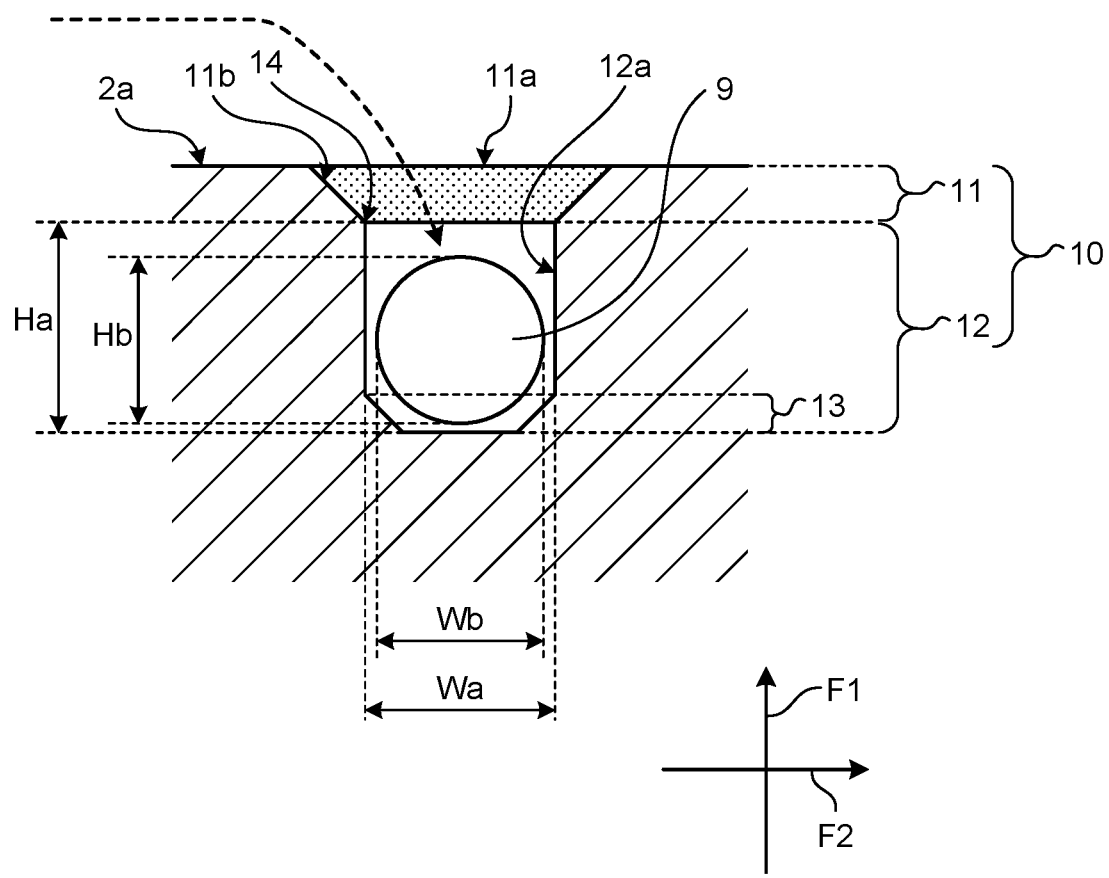
FIG. 3 is a cross-sectional schematic diagram schematically illustrating a structure of a cross section taken along a line A-A of the storage well illustrated in FIG. 2.

FIG. 2 is a diagram illustrating one configuration example of a storage well of the storage container according to the first embodiment of the present disclosure. FIG. 2 illustrates a part of the storage well extracted from the storage well group 5 of the storage container 1 according to the first embodiment viewed from their opening side (top view). FIG. 3 is a cross-sectional schematic diagram schematically illustrating a structure of a cross section taken along a line A-A of the storage well illustrated in FIG. 2.

In the present disclosure, a depth direction of the storage well is defined as a depth direction F1, for example, as illustrated in FIG. 3. In the depth direction F1, the opening side of the storage well (a side of the substrate surface 2a) is an upper side, and a bottom side of the storage well (opposite side to the substrate surface 2a) is a lower side. Moreover, a direction perpendicular to the depth direction F1 of the storage well is defined as a width direction F2, for example, as illustrated in FIG. 3. As for the width direction F2, for convenience of explanation, a right side toward the drawing is described as a positive side, and a left side is described as a negative side.

As illustrated in FIGS. 2 and 3, a storage well 10 according to the first embodiment includes an opening forming portion 11 that forms an opening portion of the storage well 10, and a storage portion 12 that removably stores an object to be stored 9 through this opening portion. In the first embodiment, the opening forming portion 11 and the storage portion 12 are made of a glass material (for example, silica glass) identical to each other.

The opening forming portion 11 constitutes an upper portion in the depth direction F1 relative to the storage portion 12, out of the storage well 10. Specifically, the opening forming portion 11 forms an opening portion 11a that opens to the substrate surface 2a as the opening portion of the storage well 10 as illustrated in FIGS. 2 and 3. Moreover, the opening forming portion 11 includes an inclined surface 11b on an inner wall of the opening portion 11a. The inclined surface 11b is a surface that is inclined downward from the substrate surface 2a in the depth direction F1 of the storage well 10 as illustrated in FIG. 3. In the first embodiment, the inclined surface 11b is formed throughout the inner wall of the opening portion 11a. That is, a size of the opening portion 11a in the width direction F2 (hereinafter, opening size as appropriate) continuously decreases as it shifts downward from the substrate surface 2a in the depth direction F1 of the storage well 10. Examples of a shape of the opening portion 11a as described include, for example, an inversed truncated cone, an inverted truncated pyramid, and the like. In FIGS. 2 and 3, an inverted truncated cone is illustrated as an example of the shape of the opening portion 11a. The inverted truncated cone is a shape in which a truncated cone is inversed upside down. Similarly, the inverted truncated pyramid is a shape in which a truncated pyramid is inversed upside down.

The storage portion 12 is a bottomed concave portion that communicates with a region on the substrate surface 2a through the opening portion 11a. Specifically, as illustrated in FIGS. 2 and 3, the storage portion 12 has a side wall surface 12a in an entire inner periphery of the storage portion 12 on a lower side relative to the opening forming portion 11 in the depth direction F1 of the storage well 10. The side wall surface 12a is formed to extend in a direction perpendicular to the substrate surface 2a. Examples of a shape of the side wall surface 12a include a shape of a cylindrical side wall shape, a shape of a prism side wall shape, and the like. In FIGS. 2 and 3, a shape of a cylindrical side wall shape is illustrated as one example of the shape of the side wall surface 12a. Moreover, the storage portion 12 includes a bottom portion 13 that is connected to a lower end of the side wall surface 12a. The bottom portion 13 has an inclination in a joint portion with the side wall surface 12a, corresponding to the inclined surface 11b described above, for example, as illustrated in FIG. 3.

Furthermore, the side wall surface 12a of the storage portion 12 is connected to the inclined surface 11b of the opening portion 11a described above as illustrated in FIGS. 2 and 3. Specifically, a lower end of the inclined surface 11b of the opening portion 11a is connected to the side wall surface 12a of the storage portion 12, forming a ridgeline 14. In the first embodiment, the lower end of the inclined surface 11b and an upper end of the side wall surface 12a coincide with each other at the ridgeline 14, and between the lower end of the inclined surface 11b and the upper end of the side wall surface 12a, a surface other than the inclined surface 11b and the side wall surface 12a (for example, a horizontal surface parallel to the substrate surface 2a, or the like) is not present.

Moreover, as illustrated in FIG. 3, the storage portion 12 stores the object to be stored 9 in inner space surrounded by the side wall surface 12a and the bottom portion 13. A depth Ha and a width Wa of the storage portion 12 forming this inner space are set to sizes suitable for storing the object to be stored 9 individually. The depth Ha of the storage portion 12 is a length in the depth direction F1 from the upper end of the side wall surface 12a to the lower end of the bottom portion 13 of the storage portion 12. The width Wa of the storage portion 12 is a length between opposite portions of the side wall surface 12a facing each other in the width direction F2 of the storage portion 12. For example, the depth Ha of the storage portion 12 is set to an appropriate value, such as a value satisfying a condition of Hb<Ha<2×Hb, based on a height Hb (length in the depth direction F1) of the object to be stored 9. The width Wa is set to an appropriate value, such as a value satisfying a condition of Wb<Wa<2×Wb, based on a width Wb (length in the width direction F2) of the object to be stored 9.

The object to be stored 9 includes a minute object, such as, a cell and a particle other than cells. Moreover, a shape of the object to be stored 9 is not limited to a spheric shale as illustrated in FIG. 3, but may be a desirable shape.

In the storage well 10 constituted of the opening forming portion 11 and the storage portion 12 described above, the object to be stored 9 is stored by a method described below. Specifically, a fluid including a larger number of the object to be stored 9 than the number of the storage wells 10 included in the storage well group 5 of the storage container 1 illustrated in FIG. 1 (for example, more than 1.5 to 2.0 times as many as the number of the storage wells 10 arranged) is prepared, and this fluid is poured on the substrate surface 2a of the storage container 1 toward the storage well group 5. Thus, the objects to be stored 9 are stored in each of the storage well group 5 from the substrate surface 2a with the fluid. At this time, for a single unit of the storage well 10, a single piece of the object to be stored 9 flows into the inside of the storage portion 12 from the substrate surface 2a through the opening portion 11a, and flowing down the inclined surface 11b with the fluid as indicated by a dashed arrow in FIG. 3.

The object to be stored 9 once stored in the storage well 10 as described above is stopped its flow (movement) by the side wall surface 12a of the storage portion 12. As a result, the object to be stored 9 is less likely to be removed from the storage well 10 unless otherwise it is intentionally removed from the storage well 10. Even if a cleaning process to remove an extra pieces of the object to be stored 9 remaining on the substrate surface 2a with a cleaning solution is performed, the object to be stored 9 in the storage well 10 remains in the storage well 10 without being flowed out of the storage well 10 by this cleaning solution.

Figure 4:
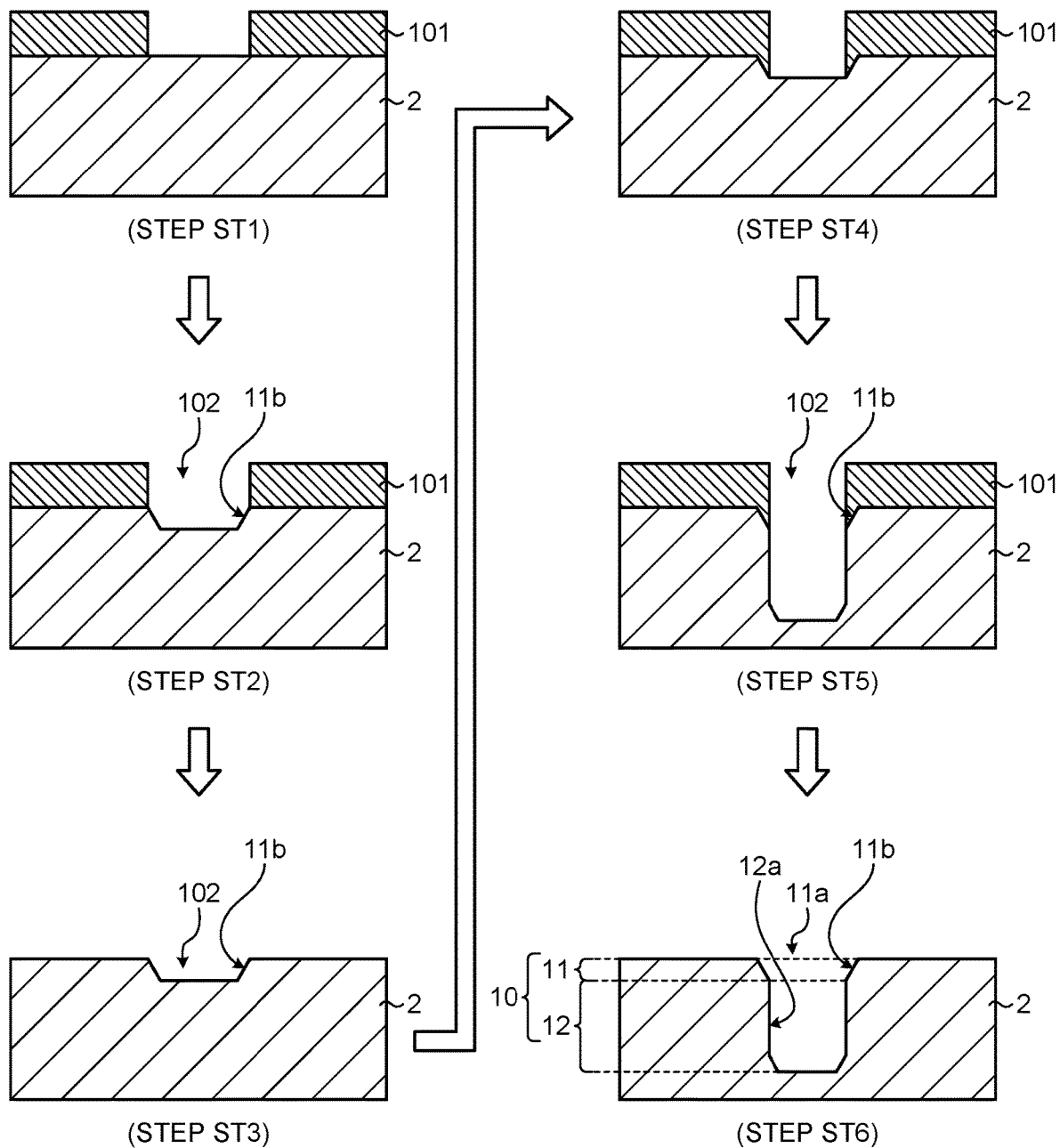
FIG. 4 is a diagram illustrating one example of a manufacturing method of the storage well according to the first embodiment.

Next, a manufacturing method of the storage well 10 according to the first embodiment will be explained. FIG. 4 is a diagram illustrating one example of the manufacturing method of the storage well according to the first embodiment. The respective storage well groups 5 of the storage container 1 are formed by a manufacturing method similar to that of this storage well 10.

As illustrated in FIG. 4, in the manufacturing method of the storage well 10, first, step ST1 of patterning a resist 101 on the substrate 2 is performed. In step ST1, the resist 101 is formed on the substrate 2 to form a pattern to expose a portion in which the storage well 10 is formed out of the substrate 2 by the photolithography technique.

After step ST1 is performed, step ST2 of forming the inclined surface 11b by etching on a portion to form an inner wall of the opening portion 11a of the storage well 10 out of the substrate 2 is performed. In step ST2, the resist 101 described above serves as a mask, and a portion not covered with the resist 101 out of the substrate 2 is subjected to wet etching. By this process, in the relevant portion of the substrate 2, the concave portion 102 having the inclined surface 11b on the inner wall is formed. This inclined surface 11b is inclined so as to slope down to a bottom surface of the concave portion 102 from a surface portion masked by the resist 101 out of the substrate 2.

After step ST2 is performed, step ST3 of removing the resist 101 is performed. In step ST3, the resist 101 is removed from the substrate 2 by predetermined resist exfoliation processing. Thus, the concave portion 102 having the inclined surface 11b on the inner wall is formed in the substrate 2.

After step ST3 is performed, step ST4 of patterning the resist 101 on the substrate 2 having the concave portion 102 is performed. In step ST4, the resist 101 is formed on the substrate 2 so as to form a pattern to expose a portion except the inclined portion 11b of the concave portion 102 (specifically, the bottom surface of the concave portion 102) out of the substrate 2 by the photolithography technique.

After step ST4 is performed, step ST5 of etching a portion other than the inclined portion 11b of the concave portion 102 out of the substrate 2 is performed. In step ST5, the resist 101 formed by step ST4 described above serves as a mask, and a portion other than the portion covered with the resist 101 out of the concave portion 102 (the inclined surface 11b and the like) is subjected to dry etching. Thus, the concave portion 102 of the substrate 2 is formed to be further deep maintaining the inclined surface 11b as illustrated in FIG. 4.

After step ST5 is performed, step ST6 of removing the resist 101 is performed, and the processing is completed. In step ST6, the resist 101 is removed from the substrate 2 by predetermined resist exfoliation processing or the like. Thus, as illustrated in FIG. 4, the storage well 10 constituted of the opening forming portion 11 having the opening portion 11a and the inclined surface 11b, and the bottomed storage portion 12 having the side wall surface 12a is formed on the substrate 2.

As explained above, in the first embodiment of the present disclosure, the storage well 10 formed in plurality on the substrate surface 2a has the inclined surface 11b that is inclined from the substrate surface 2a on the inner wall (for example, on the entire periphery of the inner wall) of the opening portion 11a of the opening forming portion 11 on a lower side in the depth direction F1 of the storage well 10, and has the bottomed storage portion 12 that is connected to the region on the substrate surface 2a through the opening portion 11a. In the storage well 10, the side wall surface 12a extends in a direction perpendicular to the substrate surface 2a, and the lower end of the inclined surface 11b is connected to the side wall surface 12a of the storage portion 12, forming the ridgeline 14.

Accordingly, because a corner portion or a protruding portion that can damage the object to be stored 9 is not present between the inclined surface 11b on the inner wall of the opening portion 11a and the side wall surface 12a of the storage portion 12, it is possible to store the intended object to be stored 9 on the substrate surface 2a easily in the inside of the storage portion 12 by guiding smoothly along the inclined surface 11b from the opening portion 11a. In addition, the vertical side wall surface 12a of the storage portion 12 can stop the flow of the object to be stored 9 that has once been stored inside the storage portion 12. As a result, unintentional displacement of the object to be stored 9 from the storage well 10 can be suppressed. From the above, it is possible to suppress the object to be stored 9 getting damaged at the time of storage, and to improve the storage efficiency of the object to be stored 9 in the storage wells 10.

Second Embodiment

Figure 5:
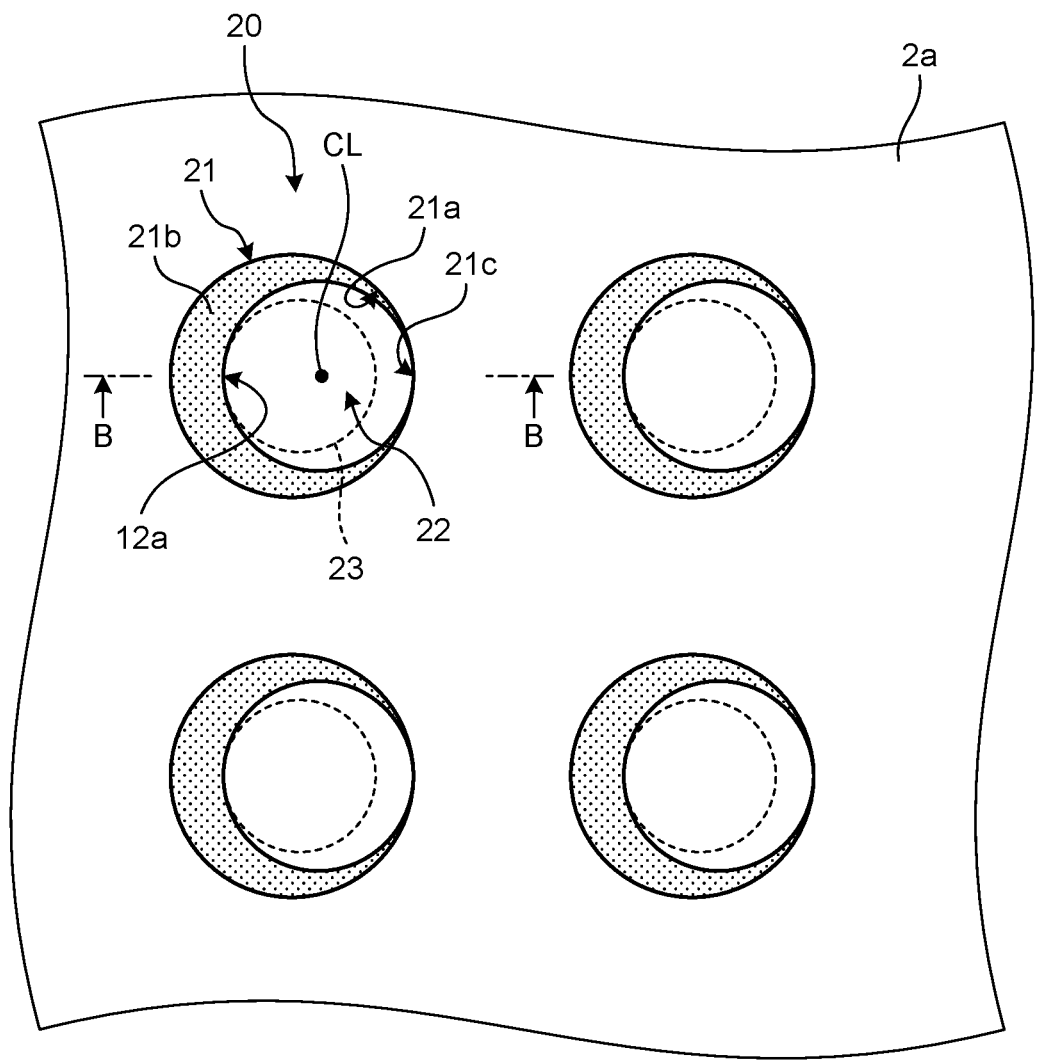
FIG. 5 is a diagram illustrating one configuration example of a storage well of a storage container according to a second embodiment of the present disclosure.
Figure 6:
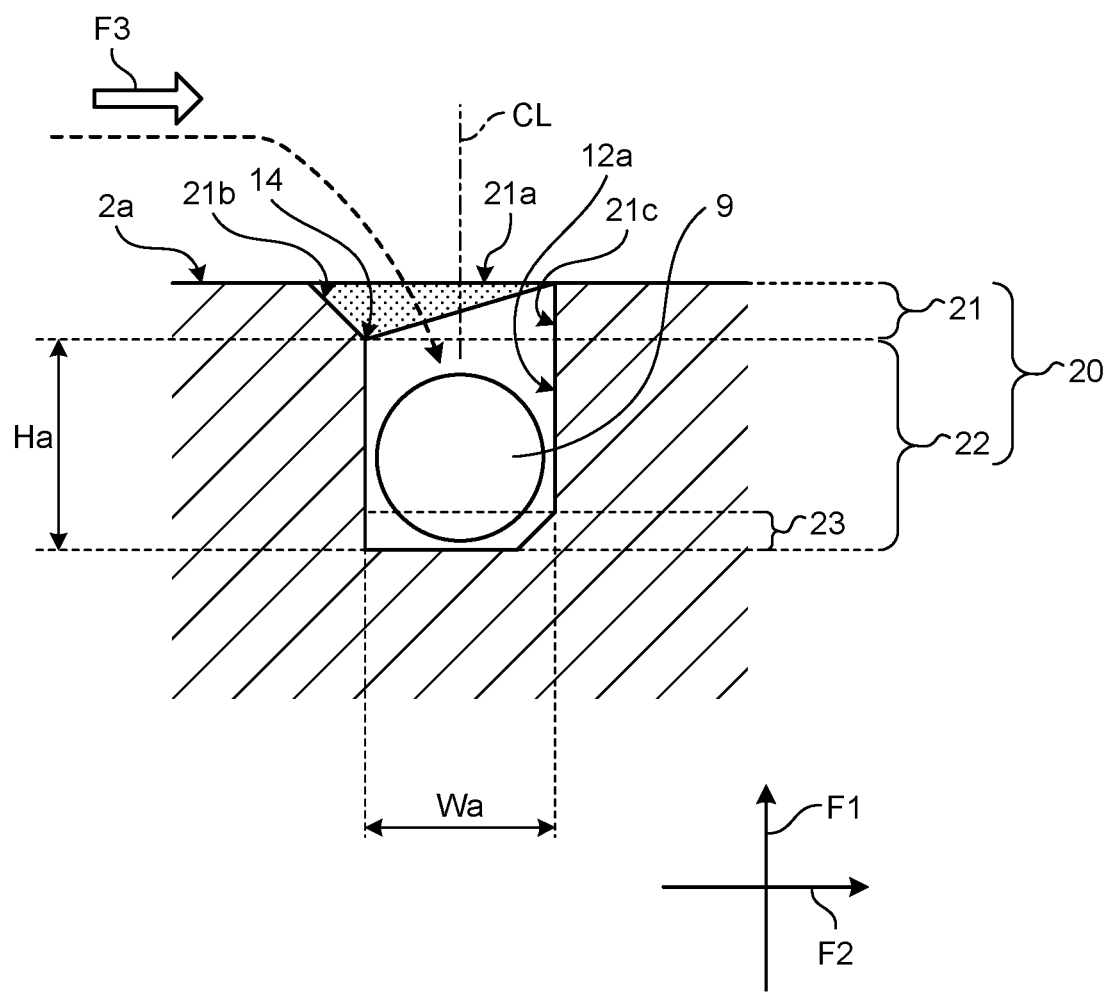
FIG. 6 is a cross-sectional schematic diagram schematically illustrating a structure of a cross section taken along a line B-B of the storage well illustrated in FIG. 5.

Next, a storage container according to a second embodiment of the present disclosure will be explained. FIG. 5 is a diagram illustrating one configuration example of a storage well of the storage container according to the second embodiment of the present disclosure. FIG. 5 illustrates some of storage wells extracted from a storage well group of the storage container according to the second embodiment viewed from their opening side. FIG. 6 is a cross-sectional schematic diagram schematically illustrating a structure of a cross section taken along a line B-B of the storage well illustrated in FIG. 5. As illustrated in FIGS. 5 and 6, a storage well 20 according to the second embodiment includes an opening forming portion 21 in place of the opening forming portion 11 of the storage well 10 according to the first embodiment described above, and includes a storage portion 22 in place of the storage portion 12. Although not particularly illustrated, the storage container according to the second embodiment includes a storage well 20 of the second embodiment in place of the storage well 10 of the first embodiment as a storage well included in the storage well group 5 (refer to FIG. 1) of the predetermined substrate surface 2a in the substrate 2. Other components are the same as those in the first embodiment, and like reference symbols are assigned to like parts.

The opening forming portion 21 forms an upper portion in the depth direction F1 above the storage portion 22 in the storage well 20. Specifically, as illustrated in FIGS. 5 and 6, the opening forming portion 21 forms an opening portion 21a that opens to the substrate surface 2a, as an opening of the storage well 20. Moreover, the opening forming portion 21 has an inclined surface 21b on an inner wall of the opening portion 21a.

The inclined surface 21b is a surface inclined downward from the substrate surface 2a in the depth direction F1 of the storage well 20 as illustrated in FIG. 6. In the second embodiment, as illustrated in FIGS. 5 and 6, the inclined surface 21b is formed, lopsided to the opposite side to an upper side-wall surface 21c described later, relative to an opening center axis CL of the opening portion 21a. That is, an opening dimension of the opening portion 21a continuously decreases as it shifts downward from the substrate surface 2a in the depth direction F1 of the storage well 20 from the substrate surface 2a in a range between the upper end and the lower end of the inclined surface 21b. Examples of a shape of the opening portion 21a as described include a shape in which an inversed truncated cone and a cylindrical shape are combined eccentrically to each other, a shape in which an inverted truncated pyramid and a prismatic shape are combined eccentrically to each other and the like. In FIGS. 5 and 6, a shape in which an inversed truncated cone and a cylindrical shape are combined eccentrically to each other is illustrated as an example of the shape of the opening portion 21a.

Moreover, the opening forming portion 21 has the upper side-wall surface 21c on an upper side relative to the side wall surface 12a of the storage portion 22 in the depth direction F1 of the storage well 20. As illustrated in FIG. 6, the upper side-wall surface 21c is formed to extend in a direction perpendicular to the substrate surface 2a in a portion lopsided to the opposite side to the inclined surface 21b relative to the opening center axis CL out of the inner wall of the opening portion 21a. In the second embodiment, the upper side-wall surface 21c is continuously integrated with the side wall surface 12a of the storage portion 22 to form the same plane.

The storage portion 22 is a bottomed concave portion that communicates with a region on the substrate surface 2a through the opening portion 21a, and that removably stores the object to be stored 9 through the opening portion 21a through the opening portion 11a. Specifically, as illustrated in FIGS. 5 and 6, the storage portion 22 has the side wall surface 12a similar to the first embodiment described above on a lower side in the depth direction F1 of the storage well 20 relative to the opening forming portion 21. Moreover, the storage portion 22 includes a bottom portion 23 that is connected to the lower end of the side wall surface 12a. The bottom portion 23 has an inclination in a joint portion with the side wall surface 12a, formed lopsided to the opposite side to the inclined surface 21b relative to the opening center axis CL of the opening portion 21a.

Moreover, the side wall surface 12a of the storage portion 22 is connected to the inclined surface 21b of the opening portion 21a described above as illustrated in FIGS. 5 and 6. Specifically, the lower end of the inclined surface 21b of the opening portion 21a, directly continues to the side wall surface 12a of the storage portion 22 forming the ridgeline 14, and continues indirectly to the side wall surface 12a of the storage portion 22 through the upper side-wall surface 21c forming the ridgeline 14. In the second embodiment, because the side wall surface 12a of the storage portion 22 is continuously integrated with the upper side-wall surface 21c to form the same plane therewith, between the lower end of the inclined surface 21b and the upper end of the side wall surface 12a, a surface other than the inclined surface 11b, the side wall surface 12a, and the upper side-wall surface 21c (for example, a horizontal surface parallel to the substrate surface 2a, or the like) is not present.

Furthermore, as illustrated in FIG. 6, the storage portion 22 stores the object to be stored 9 in inner space surrounded by the side wall surface 12a and the bottom portion 23. The depth Ha and the width Wa of the storage portion 22 to form this inner space are set to dimensions suitable for storing the object to be stored 9 individually, similarly to the first embodiment described above.

In the storage well 20 constituted of the opening forming portion 21 and the storage portion 22 described above, the object to be stored 9 is stored by a method similar to that of the first embodiment. For example, a fluid including plural pieces of the object to be stored 9 (not illustrated) is poured in a predetermined direction F3 (refer to FIG. 6) along the substrate surface 2a. Thus, the objects to be stored 9 are stored in each of the storage well group 5 (refer to FIG. 1) from the substrate surface 2a with the fluid. At this time, for a single unit of the storage well 20, a single piece of the object to be stored 9 flows into the inside of the storage portion 22 from the substrate surface 2a through the opening portion 21a, and down the inclined surface 21b with the fluid as indicated by a dashed arrow in FIG. 6.

As described, the object to be stored 9 that has once been stored in the storage well 20 as described above is stopped its flow (movement) by the side wall surface 12a of the storage portion 22 and the upper side-wall surface 21c. This stopping effect for a flow of the object to be stored 9 is improved by arranging the upper side-wall surface 21c above of the side wall surface 12a, compared with a case of arranging only the side wall surface 12a. As a result, the object to be stored 9 is even less likely to be removed from the storage well 10 unless otherwise it is intentionally removed from the storage well 20. Even if a cleaning process to remove an extra pieces of the object to be stored 9 remaining on the substrate surface 2a with a cleaning solution is performed, the object to be stored 9 in the storage well 20 remains in the storage well 20 without being flowed out of the storage well 20 by this cleaning solution (especially a cleaning solution flowing in the predetermined direction F3).

Figure 7:
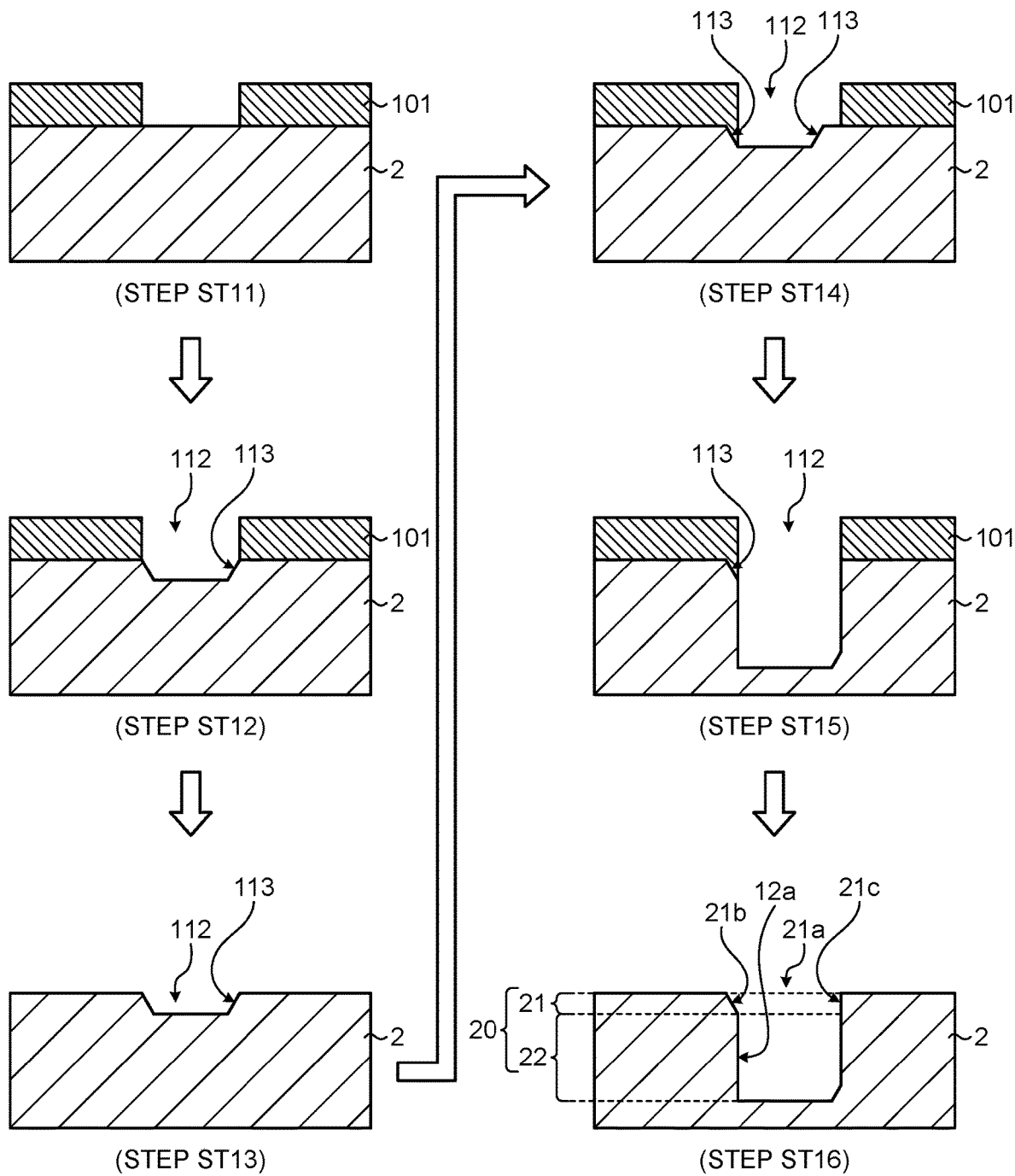
FIG. 7 is a diagram illustrating one example of a manufacturing method of the storage well according to the second embodiment.

Next, a manufacturing method of the storage well 20 according to the second embodiment will be explained. FIG. 7 is a diagram illustrating one example of the manufacturing method of the storage well according to the second embodiment. The respective storage well groups 5 of the storage container according to the second embodiment are formed by a manufacturing method similar to that of this storage well 20.

As illustrated in FIG. 7, in the manufacturing method of the storage well 20, first, step ST11 of patterning the resist 101 on the substrate 2 is performed. In step ST11, the resist 101 is formed on the substrate 2 to form a pattern to expose a portion in which the storage well 20 is formed out of the substrate 2 by the photolithography technique.

After step ST11 is performed, step ST12 of forming an inclined surface 113 by etching is performed on a portion to form an inner wall of the opening portion 21a of the storage well 20 out of the substrate 2. In step ST12, the resist 101 described above serves as a mask, and a portion not covered with the resist 101 out of the substrate 2 is subjected to wet etching. By this process, in the relevant portion of the substrate 2, concave portion 112 having the inclined surface 113 on the inner wall is formed as illustrated in FIG. 7. This inclined surface 113 is inclined so as to slope down to a bottom surface of the concave portion 112 from a surface portion masked with the resist 101 out of the substrate 2.

After step ST12 is performed, step ST13 of removing the resist 101 is performed. In step ST13, the resist 101 is removed from the substrate 2 by predetermined resist exfoliation processing. Thus, the concave portion 112 having an inclined surface 114 on the inner wall is formed in the substrate 2.

After step ST13 is performed, step ST14 of patterning the resist 101 on the substrate 2 having the concave portion 102 is performed. In step ST14, the resist 101 is formed on the substrate 2 so as to form a pattern to expose a portion except the bottom portion and one side of the inclined portion 113 of the concave portion 112 (In FIG. 7, the right side of the sheet) out of the substrate 2, and to cover the other portions (including the other side of the inclined surface 113) by the photolithography technique.

After step ST14 is performed, step ST15 of etching an exposed, such as the concave portion 102, out of the substrate 2 is performed. In step ST15, the resist 101 formed by step ST14 described above serves as a mask, and a portion other than the portion covered with the resist 101 out of the concave portion 112 (in FIG. 7, a portion of the inclined surface 113 on a left side of the sheet) is subjected to dry etching. Thus, the concave portion 112 of the substrate 2 is formed to be further deep maintaining the masked portion in the inclined surface 113.

After step ST15 is performed, step ST16 of removing the resist 101 is performed, and the processing is completed. In step ST16, the resist 101 is removed from the substrate 2 by predetermined resist exfoliation processing or the like. Thus, as illustrated in FIG. 7, the storage well 20 constituted of the opening forming portion 21 having the opening portion 21a, the inclined surface 21b, and the upper side-wall surface 21c, and the bottomed storage portion 22 having the side wall surface 12a is formed on the substrate 2.

As explained above, in the second embodiment of the present disclosure, in a portion on the upper side in the depth direction F1 of the storage well 20 relative to the side wall surface 12a of the storage portion 22 out of the inner wall of the opening portion 21a of the opening forming portion 21 of the storage well 20, the upper side-wall surface 21c that extends in a direction perpendicular to the substrate surface 2a is formed, and in a portion lopsided to the opposite side to the upper side-wall surface 21c relative to the opening center axis CL of the opening portion 21a, the inclined surface 21b that is inclined from the substrate surface 2a on the lower side in the depth direction F1 of the storage well 20 is formed, and other portions are structured similarly to the first embodiment.

Accordingly, while obtaining the effect similar to the case of the first embodiment described above, because the effect of suppressing flowing out of the object to be stored 9 that has once been stored in the storage well 20 can be improved with the upper side-wall surface 21c, it is possible to strongly suppress unintentional displacement of the object to be stored 9 from the storage well 20 while maintaining ease of storing (flowing) the object to be stored 9 into the storage well 20, and to improve the storage efficiency of the object to be stored 9 in the storage wells 20.

Third Embodiment

Figure 8:
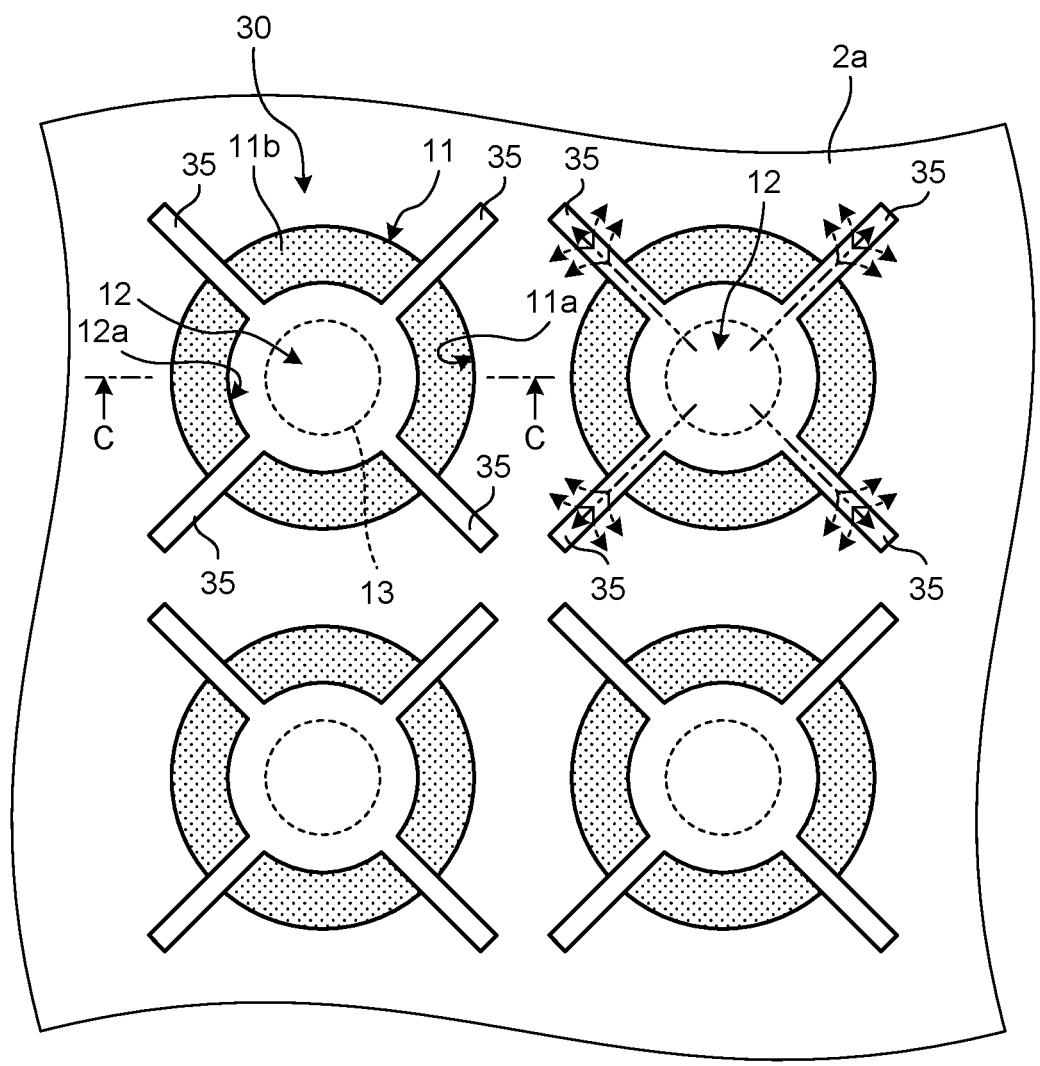
FIG. 8 is a diagram illustrating one configuration example of a storage well of a storage container according to a third embodiment of the present disclosure.
Figure 9:
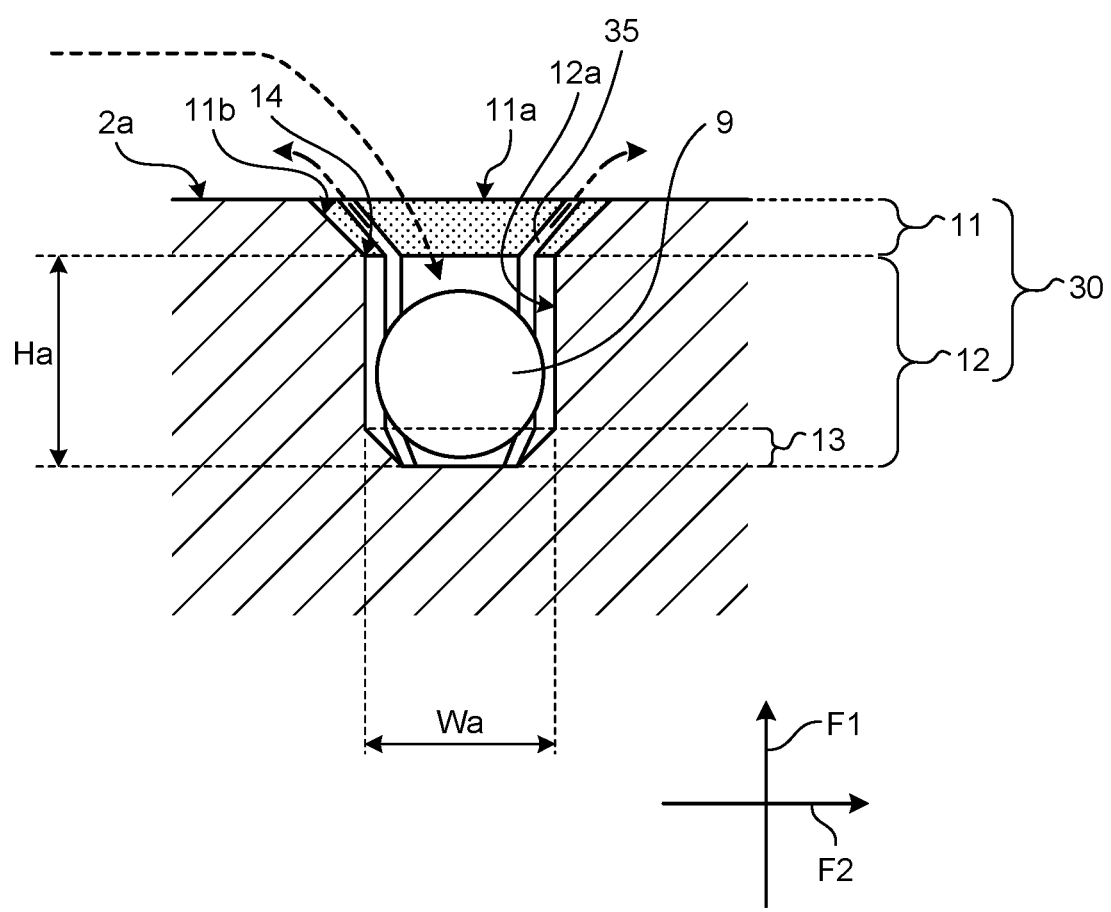
FIG. 9 is a cross-sectional schematic diagram schematically illustrating a structure of a cross section taken along a line C-C of the storage well illustrated in FIG. 8.

Next, a storage container according to a third embodiment of the present disclosure will be explained. FIG. 8 is a diagram illustrating one configuration example of a storage well of the storage container according to a third embodiment of the present disclosure. FIG. 8 illustrates some of storage wells extracted from a storage well group of the storage container according to the third embodiment viewed from their opening side. FIG. 9 is a cross-sectional schematic diagram schematically illustrating a structure of a cross section taken along a line C-C of the storage well illustrated in FIG. 8. As illustrated in FIGS. 8 and 9, a storage well 30 according to the third embodiment further includes a fluid flow-out portion 35 in addition to the components similar to those of the storage well 10 according to the first embodiment described above. Although not particularly illustrated, the storage container according to the third embodiment includes the storage well 30 of the third embodiment in place of the storage well 10 of the first embodiment described above as the storage well included in the storage well group 5 (refer to FIG. 1) on the predetermined substrate surface 2a in the substrate 2. Other components are the same as those of the first embodiment, and like reference signs are assigned to like parts.

The fluid flow-out portion 35 is to let a fluid accumulated inside the storage well 30 flow out to the outside. Specifically, as illustrated in FIGS. 8 and 9, the fluid flow-out portion 35 forms space having a slit shaped cross-section in a depth reaching the bottom portion 13 of the storage portion 12 from the substrate surface 2a, and is arranged to extend from the storage portion 12 of the storage well 30 to a portion outside the opening portion 11a in the substrate 2 (refer to FIG. 1) in the desirable number. For example, in the third embodiment, the fluid flow-out portion 35 is arranged in plurality (four in FIG. 8) around the center axis in the depth direction F1 of the storage well 30 keeping a predetermined interval. Moreover, a depth of the fluid flow-out portion 35 (distance between the upper end and the lower end in the depth direction F1) is the same depth as the storage well 30.

Furthermore, respective portions on the storage portion 12 side, on the inner wall side of the opening portion 11a (that is the inclined surface 11b side), and the substrate surface 2a side in the fluid flow-out portion 35 are connected to one another and are open. An opening size of respective opening portions of this fluid flow-out portion 35 is small compared to the size of the object to be stored 9 (width, height, and the like). The fluid flow-out portion 35 as described communicates with the storage portion 12 of the storage well 30, and is capable of letting a fluid that has flowed into the storage portion 12 from the opening portion 11a flow out to the outside. Moreover, the object to be stored 9 cannot flow to the inside of the fluid flow-out portion 35.

The fluid flow-out portion 35 described above can be formed, for example, by patterning the resist 101 to expose a portion in which the fluid flow-out portion 35 is formed and the like out of the substrate 2, and etching this portion together with a concave portion 102 in the processes ST4 to ST5 in FIG. 4.

In the storage well 30 according to the third embodiment, the object to be stored 9 is stored by a method similar to that of the first embodiment. For example, a fluid including plural pieces of the object to be stored 9 (not illustrated) is poured on the substrate surface 2a toward the storage well group 5 (refer to FIG. 1). Thus, the objects to be stored 9 are stored in each of the storage well groups 5 from the substrate surface 2a with the fluid. At this time, for a single unit of the storage well 30, a single piece of the object to be stored 9 flows into the inside of the storage portion 12 from the substrate surface 2a through the opening portion 11a, and flowing down the inclined surface 11b with the fluid as indicated by a dashed arrow in FIG. 9.

The object to be stored 9 that has once been stored in the storage well 30 as described is less likely to be removed from the storage well 30 unless otherwise it is intentionally removed from the storage well 30 because a flow (movement) is stopped by the side wall surface 12a of the storage portion 12 similarly to the case of the first embodiment described above. Even if a cleaning process to remove an extra pieces of the object to be stored 9 remaining on the substrate surface 2a with a cleaning solution is performed, the object to be stored 9 in the storage well 30 remains in the storage well 30 without being flowed out of the storage well 30 by this cleaning solution.

On the other hand, at the time of storing the object to be stored 9 into the storage well 30, there is a case in which a fluid to flow the object to be stored 9 into the inside of the storage well 30 (particularly, the inside of the storage portion 12) has flowed therein prior to the object to be stored 9, to be in a filled state. If the object to be stored 9 is to be stored in a storage well not having the fluid flow-out portion 35 described above, to make the object to be stored 9 flow into the inside of the storage well that has already been filled with a fluid, it is necessary to make the fluid flow out from a gap between the sided wall surface of the storage well and an outer surface of the object to be stored 9. In this case, because the gap is very small (for example, a size of micron order), it can be difficult to make the object to be stored 9 flow into the inside of the storage well while making the fluid flow out to the outside.

On the other hand, in the storage well 30 having the fluid flow-out portion 35 described above, a fluid filled in the storage portion 12 flows out to the substrate surface 2a outside the storage well 30 passing through the fluid flow-out portion 35 from the inside of the storage portion 12 as indicated by an alternate long and two short dashes arrow in FIGS. 8 and 9. Thus, flow-in (storage) of the object to be stored 9 to the storage portion 12 becomes less likely to be hampered by the fluid in the storage portion 12.

As explained above, in the third embodiment of the present disclosure, the fluid flow-out portion 35 that communicates with the storage portion 12 of the storage well 30 is arranged, and it is configured to make the fluid that has flowed into the storage portion 12 flow out to the outside of the storage portion 12 from the fluid flow-out portion 35, and the other components are structured similarly to the first embodiment. Therefore, while obtaining an effect similar to that of the first embodiment described above, it is possible to let the object to be stored 9 flow into the inside of the storage portion 12 from the opening portion 11a while letting the fluid accumulated in the inside of the storage portion 12 flow out to the outside from the fluid flow-out portion 35. As a result, because a flow of the object to be stored 9 into the storage portion 12 becomes less likely to be hampered by the fluid even if the storage portion 12 is filled with the fluid, it is easy to store the object to be stored 9 into the storage portion 12.

First Modification of Third Embodiment

Figure 10:
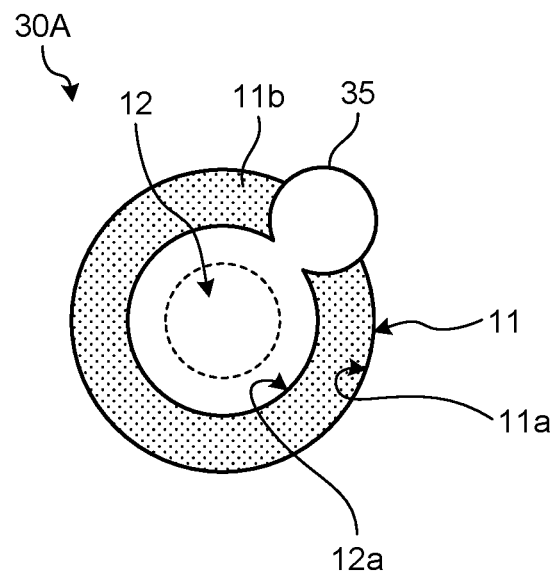
FIG. 10 is a diagram illustrating one configuration example of a storage well according to a first modification of the third embodiment of the present disclosure.

Next, a first modification of the storage well according to the third embodiment of the present disclosure will be explained. FIG. 10 is a diagram illustrating one configuration example of a storage well according to the first modification of the third embodiment of the present disclosure. FIG. 10 illustrates a storage well 30A according to this first modification viewed from its opening side.

The fluid flow-out portion 35 described above is not limited to be the one forming space having a cross-section in a slit shape as illustrated in FIGS. 8 and 9, but may be ones in other shapes. For example, as illustrated in FIG. 10, the storage well 30A according to the first modification has the fluid flow-out portion 35 forming space in a cylindrical shape. The fluid flow-out portion 35 of the first embodiment is open in a part of the side wall surface 12a throughout the depth direction of the storage portion 12, and communicates with the storage portion 12 through this opening. Moreover, an upper end of the fluid flow-out portion 35 opens in a range from the inclined surface 11b through to the outside of the opening portion 11a in the opening forming portion 11, and communicates with the outside of the storage well 30A through this opening. The fluid flow-out portion 35 as described can increase a capacity of inner space communicating with the storage portion 12 to be larger than a capacity of a single unit of the one having a slit-shaped cross-section described above, while maintaining a size of the opening to the storage portion 12 being about the same as that of the one having a slit-shaped cross-section described above.

Because the storage well 30A according to the first modification can also let a fluid that has flowed into the storage portion 12 flow out to the outside of the storage portion 12 from the fluid flow-out portion 35, an effect similar to that of the third embodiment described above can be obtained.

Second Modification of Third Embodiment

Figure 11:
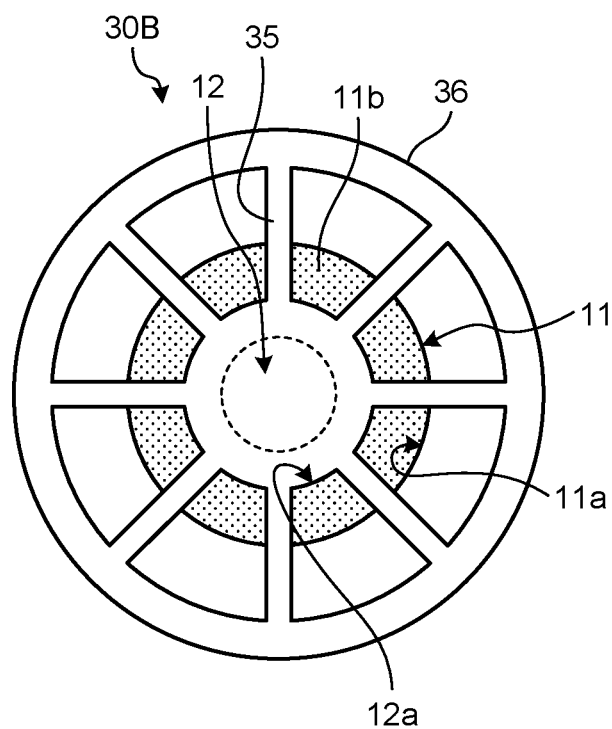
FIG. 11 is a diagram illustrating one configuration example of a storage well according to a second modification of the third embodiment of the present disclosure.

Next, a second modification of the storage well according to the third embodiment of the present disclosure will be explained. FIG. 11 is a diagram illustrating one configuration example of a storage well according to the second modification of the third embodiment of the present disclosure. FIG. 11 illustrates a storage well 30B according to the second modification viewed from its opening side.

The number of the fluid flow-out portion 35 described above is not limited to four as illustrated in FIG. 8, and the respective units of the fluid flow-out portions 35 may communicate with one another with parts, such as respective outer ends of these, or the like. For example, as illustrated in FIG. 11, the storage well 30B according to the second modification includes plural units (eight in FIG. 11) of the fluid flow-out portion 35 having a structure similar to that of the third embodiment, and a ring-shaped groove 36 through which the respective outer ends of these fluid flow-out portions 35 communicate with one another. The ring-shaped groove 36 is one example of a groove portion to connect the respective fluid flow-out portions 35. Specifically, the ring-shaped groove 36 is a bottomed groove portion forming a ring that surrounds the opening forming portion 11 and the storage portion 12, opens to the substrate surface 2a side (refer to FIG. 8), and communicates with the outside of the storage well 30B through this opening. Moreover, the ring-shaped groove 36 has an opening at each portion corresponding to each outer end of the fluid flow-out portions 35, and is connected to the fluid flow-out portions 35 through these openings. The ring-shaped groove 36 as described enables to increase a total capacity of the fluid flow-out portions 35, while maintaining the size and the shape of the respective fluid flow-out portions 35.

Because the storage well 30B according to the second modification can also let a fluid that has flowed into the storage portion 12 flow out to the outside of the storage portion 12 from the fluid flow-out portion 35 and the ring-shaped groove 36, an effect similar to that of the third embodiment described above can be obtained.

Fourth Embodiment

Figure 12:
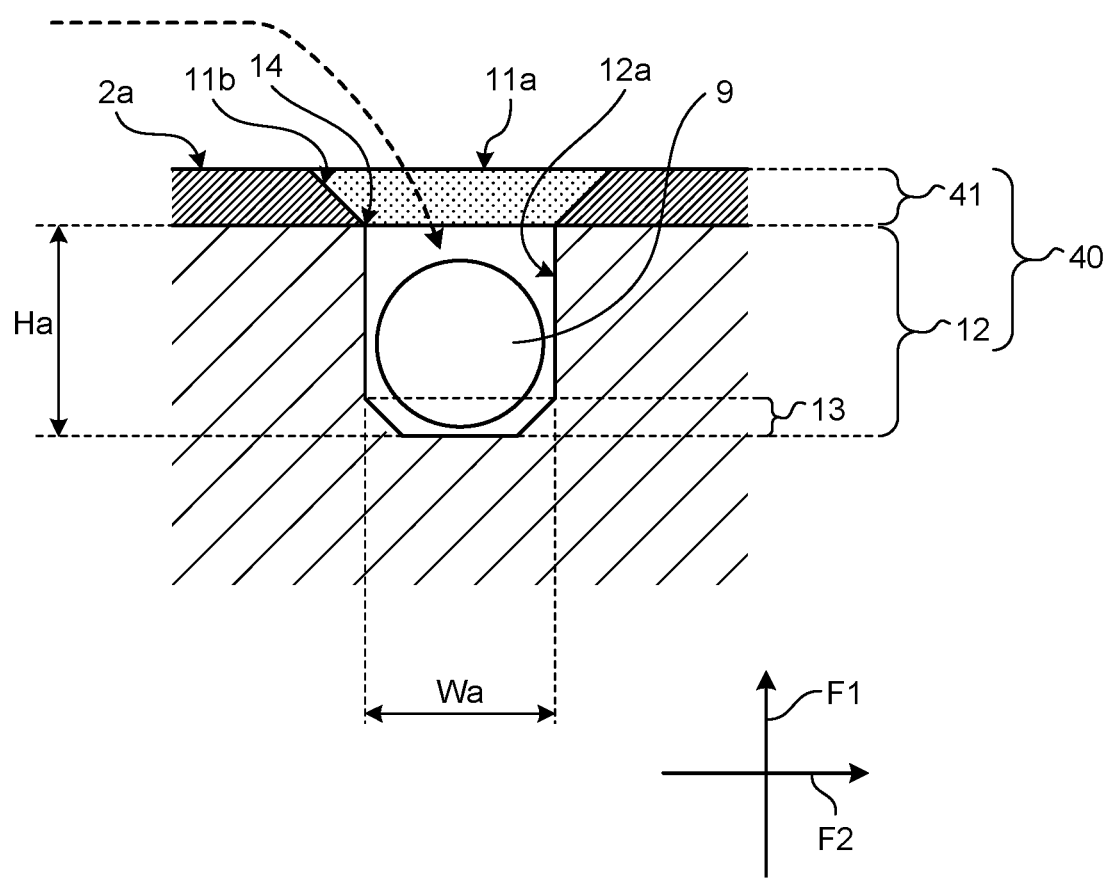
FIG. 12 is a diagram illustrating one configuration example of a storage well of a storage container according to a fourth embodiment of the present disclosure.

Next, a storage container according to a fourth embodiment of the present disclosure will be explained. FIG. 12 is a diagram illustrating one configuration example of a storage well of a storage container according to the fourth embodiment of the present disclosure. FIG. 12 illustrates a side cross-section of some of storage wells extracted from a storage well group of the storage container according to the fourth embodiment. As illustrated in FIG. 12, a storage well 40 according to the fourth embodiment includes an opening forming portion 41 in place of the opening forming portion 11 of the storage well 10 according to the first embodiment described above. Although not particularly illustrated, the storage container according to the fourth embodiment includes the storage well 40 according to the fourth embodiment in place of the storage well 10 of the first embodiment described above as a storage well included in the storage well group (refer to FIG. 1) on the predetermined substrate surface 2a in the substrate 2. Other components are the same as those of the first embodiment described above, and like reference signs are assigned to like parts.

The opening forming portion 41 is made of a glass material different from the storage portion 12. For example, the storage portion 12 is made of a pure-silica glass. In the present disclosure, pure-silica glass refers to silica glass in which the concentration of in unintentionally included purity is 0.1 mol % or lower. When an impurity is intentionally added to silica glass, the concentration of this impurity intentionally added to pure-silica glass is 1.0 mol % to 25 mol %. On the other hand, the opening forming portion 41 is made of silica glass in which a predetermined dopant material is doped, for example, zirconia ($ZrO_2$) doped silica glass (hereinafter, referred to as zirconia-doped glass, as appropriate). A dopant ratio (content rate) of zirconia in the zirconia-doped glass forming the opening forming portion 41 is several mol % or lower to mass or volume of entire silica glass to be doped. The opening forming portion 41 is same as the opening forming portion 11 in the first embodiment described above except that the material differs from the storage portion 12 as described above, and forms the opening portion 11a that opens to the substrate surface 2a and has the inclined surface 11b on the inner wall of the opening portion 11a as illustrated in FIG. 12. As a dopant material of silica glass forming the opening forming portion 41, for example, hafnia ($HfO_2$), alumina ($Al_2O_3$), and the like can be used other than zirconia, but zirconia is particularly preferable.

The substrate 2 (refer to FIG. 1) in which plural units of the storage wells 40 having the storage portion 12 and the opening forming portion 41 made of materials different from each other as one of the storage well group 5 is a laminated substrate in which a glass film (zirconia-doped glass film) that is made of zirconia-dope glass is formed on a glass substrate that is made of a glass material, such as silica class. That is, in the fourth embodiment, the substrate surface 2a illustrated in FIG. 12 is a surface of the zirconia-dope glass film in which the opening forming portion 41 is arranged.

Figure 13:
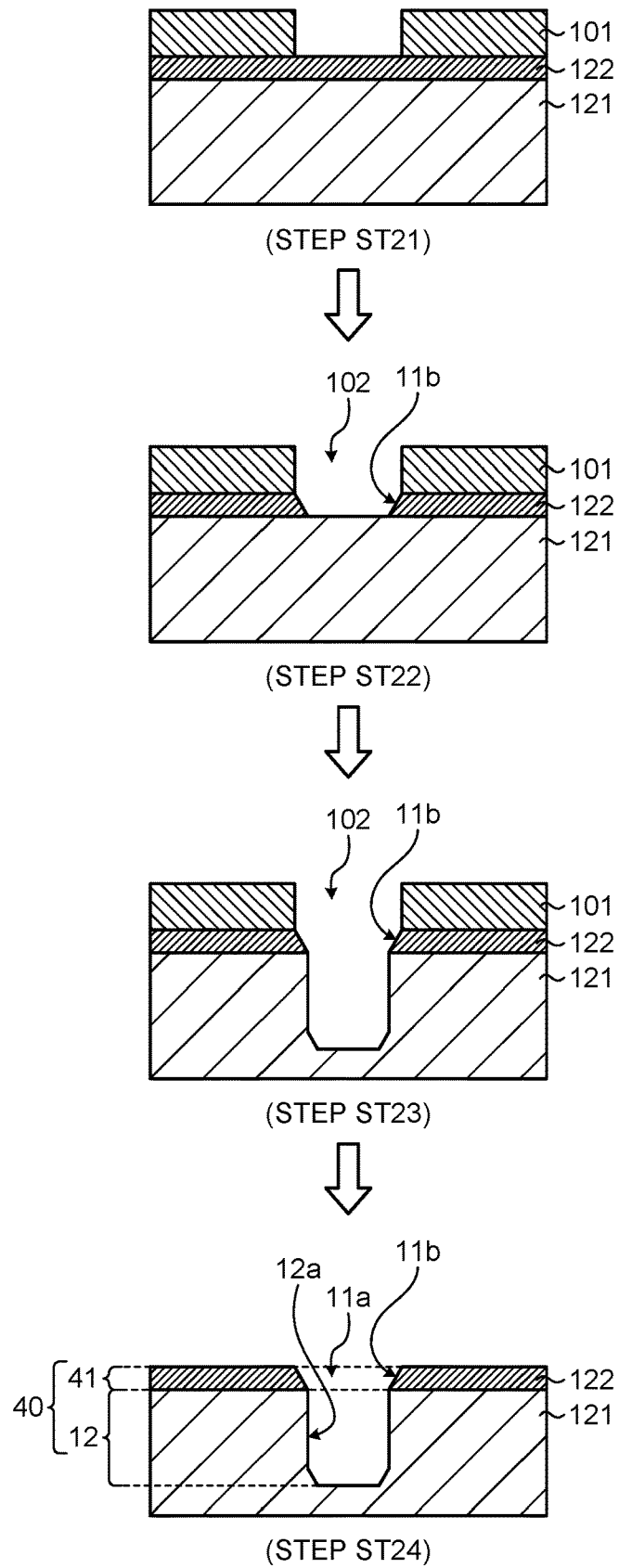
FIG. 13 is a diagram illustrating one example of a manufacturing method of a storage well according to the fourth embodiment of the present disclosure.

Next, a manufacturing method of the storage well 40 according to the fourth embodiment of the present disclosure will be explained. FIG. 13 is a diagram illustrating one example of a manufacturing method of the storage well according to the fourth embodiment of the present disclosure. The respective storage well groups 5 of the storage container according to the fourth embodiment are formed by a manufacturing method similar to that of this storage well 40. Although the manufacturing method of the storage well according to the fourth embodiment will be explained with zirconia-dope glass as silica glass forming the opening forming portion 41 as an example below, this manufacturing method is the same also when the dopant material of the silica glass is other than zirconia (for example, hafnia, alumina or the like).

As illustrated in FIG. 13, in the manufacturing method of the storage well 40, first, step ST21 of patterning the resist 101 on a surface of a zirconia-doped glass film 122 formed on a glass substrate 121 made of pure-silica glass is performed. In step ST21, the resist 101 is formed on the zirconia-doped glass film 122 to form a pattern to expose a portion in which the storage well 40 is formed out of the zirconia-doped glass film 122 by the photolithography technique.

After step ST21 is performed, step ST22 of etching the zirconia-doped glass film 122 in the pattern of the resist 101 is performed. In step ST22, the resist 101 formed by step ST21 serves as a mask, and a portion not covered with the resist 101 out of the zirconia-doped glass film 122 is subjected to dry etching. By this process, in the relevant portion of the zirconia-doped glass film 122, the concave portion 102 having the inclined surface 11b on the inner wall is formed as illustrated in FIG. 13. This inclined surface 11b is inclined so as to slope down to a bottom surface of the concave portion 102 from a surface portion masked with the resist 101 out of the zirconia-doped glass film 122. Moreover, at a stage of step ST22, a bottom surface of the concave portion 102 is an exposed surface of the glass substrate 121 that has been exposed by dry etching of the zirconia-doped glass film 122.

When dry etching is performed on a exposed portion patterned by the resist 101 out of the zirconia-doped glass film 122, an etching speed of this exposed portion tends to become slower as it approaches a mask side (a side covered with the resist 101) from a center side of this exposed portion. That is, the zirconia-doped glass film 122 has characteristics that it is easy to form an inclined surface that slopes down toward the center side from the mask side when dry etching is performed. Therefore, in the exposed portion of the zirconia-doped glass film 122, the etching depth in apportion on the center side increases, and the inclined surface 11b (refer to FIG. 13) in a form described above is formed in a portion on the mask side by dry etching.

Subsequent to step ST22, step ST23 of etching the concave portion 102 described above is performed. In step ST23, the resist 101 described above continuously serves as a mask, and a portion exposed in a pattern from the resist 101, that is, the concave portion 102 formed by step ST22, out of the glass substrate 121 and the zirconia-doped glass film 122 is further subjected to dry etching. Thus, the concave portion 102 is formed further deep as the etching depth of the glass substrate 121 increases, while maintaining the inclined surface 11b in the portion of the zirconia-doped glass film 122.

In the fourth embodiment, because step ST22 and step ST23 described above are dry etching with the resist 101 of the same pattern using as a mask, the steps are successively performed by one dry etching.

After step S23 is performed, step S24 of removing the resist 101 is performed, and the processing is completed. In step ST24, the resist 101 is removed from the zirconia-doped glass film 122 by predetermined resist exfoliation processing. Thus, the storage well 40 that is constituted of the opening forming portion 41 having the opening portion 11a and the inclined surface 11b in a portion of the zirconia-doped glass film 122, and the bottomed storage portion 12 having the side wall surface 12a in a portion of the glass substrate 121 is formed in the substrate (laminated substrate of the glass substrate 121 and the zirconia-doped glass film 122).

As explained above, in the fourth embodiment of the present disclosure, the opening forming portion 41 having the opening portion 11a that opens to the substrate surface 2a and the inclined surface 11b that is inclined from the substrate surface 2a downward I the depth direction F1 is made of silica glass doped with a dopant material, such as zirconia, and others are formed similarly to the first embodiment.

Accordingly, while obtaining an effect similar to those of the first embodiment described above, because the opening portion 11a, the inclined surface 11b, and the storage portion 12 of the storage well 40 can be successively formed by dry etching, wet etching process to form an opening and an inclined surface and a resist forming process and removing process to perform this wet etching can be omitted from the manufacturing process of the storage well 40 and, as a result, time and effort for the manufacturing of the storage well 40 can be reduced, and the storage well 40 can be formed easily.

In the first to the fourth embodiments described above, a storage well having an opening portion and a storage portion, a shape viewed from above (shape viewed from the opening side) of which is a circular shape has been described as an example, but the present disclosure is not limited thereto. In the present disclosure, shape viewed from above of an opening portion and a storage portion of a storage well may be a desirable shape, such as a circular shape, an oval shape, and a polygonal shape, suitable for a shape of an object to be store, a use, or the like. Furthermore, shapes viewed from above of the opening portion and the storage portion may be an identical shape to each other, or different shapes from each other.

Moreover, in the second embodiment described above, a material of the opening forming portion 21 having the opening portion 21a, the inclined surface 21b, and the upper side-wall surface 21c is the same as the material (for example, silica glass) of the storage portion 22, but the present disclosure is not limited thereto. In the present disclosure, a material of the opening forming portion 21 may be silica glass doped with a dopant material, such as zirconia, similarly to the fourth embodiment described above, to be different from the material of the storage portion 22.

Moreover, in the third embodiment and the first and the second modifications described above, the fluid flow-out portion that communicates with the storage portion of the storage well formed on the inclined surface throughout the inner wall periphery of the opening portion has been described as an example, but the present disclosure is not limited thereto. In the present disclosure, the fluid flow-out portion may be one that communicates with the storage portion of the storage well an inclined surface and an upper side-wall surface are formed on an inner wall of an opening portion, or may be one that communicates with a storage portion of a storage well having an opening forming portion made of zirconia-dope silica glass. That is, the storage well according to the present disclosure may be one in which the first embodiment, the third embodiment, and the first and the second modifications are appropriately combined, one in which the second embodiment, the third embodiment, and the first and the second modifications are appropriately combined, or one in which the fourth embodiment, the third embodiment, and the first and the second modifications are appropriately combined.

Furthermore, in the second modification of the third embodiment described above, a case in which the respective outer ends of the plural fluid flow-out portions 35 are connected to one another through the ring-shaped groove 36 has been described as an example, the present disclosure is not limited thereto. For example, the plural fluid flow-out portions 35 may be connected to by the ring-shaped groove 36 at a middle portion between the opening forming portion 11 side and the outer end. Moreover, a groove to connect the respective fluid flow-out portions 35 may be not in a ring shape, and the plural fluid flow-out portions 35 connected to one another by the groove are not limited to form space having a slit-shaped cross-section, but may be one forming space, for example, in a cylindrical shape as illustrated in FIG. 1, or the like.

According to an embodiment, an effect of suppressing an object to be stored getting damaged at the time of storage, and of improving the storage efficiency of an object to be stored in multiple storage wells can be produced.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A storage container comprising:
a substrate having a plurality of storage wells to store an object therein, the storage wells being formed on a predetermined substrate surface of the substrate, wherein
the storage wells each includes
an opening forming portion that forms an opening portion opening on the substrate surface, and that has an inclined surface that inclines from the substrate surface downward in a depth direction of the storage well on an inner surface of the opening portion; and
a bottomed storage portion that has a side wall surface extending in a direction perpendicular to the substrate surface on a lower side in the depth direction of the storage well relative to the opening forming portion, and that communicates with a region on the substrate surface through the opening portion, and
a lower end of the inclined surface is connected to the side wall surface of the storage portion, forming a ridgeline
a fluid flow-out portion that communicates with the storage portion, and that lets a fluid that has flowed into the storage portion flow out to an outside of the storage portion wherein the fluid flow-out portion is arranged to form space having any one of a slit-shaped cross-section and a cylindrical shape.

2. The storage container according to claim 1, wherein the inclined surface is formed throughout the inner wall of the opening portion.

3. The storage container according to claim 1, wherein the opening forming portion has an upper side-wall surface that extends in a direction perpendicular to the substrate surface on an upper side in a depth direction of the storage well relative to the side wall surface of the storage portion, and the inclined surface is formed in a lopsided manner to an opposite side to the upper side-wall surface relative to an opening center axis of the opening portion.

4. The storage container according to claim 1, wherein a depth of the fluid flow-out portion is a same as a depth of the storage well.

5. The storage container according to claim 1, further comprising:

a plurality of the fluid flow-out portions; and a groove portion that connects the fluid flow-out portions.

6. The storage container according to claim 1, wherein the opening forming portion is made of silica glass doped with zirconia, and the storage portion is made of pure-silica glass, concentration of an impurity unintentionally included in the pure-silica glass is 0.1 mol % or lower.

\* \* \* \* \*